(12) United States Patent
Kulprathipanja et al.

(10) Patent No.: US 8,203,028 B2
(45) Date of Patent: Jun. 19, 2012

(54) PROCESSES FOR OLEFIN/PARAFFIN SEPARATION UTILIZING POROUS, HYDROPHOBIC POLY(ETHER ETHER KETONE) MEMBRANES

(75) Inventors: Santi Kulprathipanja, Inverness, IL (US); Chunqing Liu, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 218 days.

(21) Appl. No.: 12/788,595

(22) Filed: May 27, 2010

(65) Prior Publication Data

US 2011/0295052 A1    Dec. 1, 2011

(51) Int. Cl.
  *C07C 7/144*    (2006.01)
(52) U.S. Cl. ........................................ 585/818; 585/809
(58) Field of Classification Search .................. None
  See application file for complete search history.

(56) References Cited

U.S. PATENT DOCUMENTS

| | | | |
|---|---|---|---|
| 4,214,020 A | 7/1980 | Ward et al. | |
| 5,107,058 A | 4/1992 | Chen et al. | |
| 5,205,968 A | 4/1993 | Damrow et al. | |
| 6,368,382 B1 | 4/2002 | Chiou | |
| 7,176,273 B2 | 2/2007 | Yuan et al. | |
| 7,250,545 B2 | 7/2007 | Roman et al. | |
| 7,361,800 B2 | 4/2008 | Herrera et al. | |
| 7,368,526 B2 | 5/2008 | Yuan et al. | |
| 2006/0201884 A1 | 9/2006 | Kulprathipanja et al. | |
| 2007/0135670 A1 | 6/2007 | Roman et al. | |
| 2008/0167512 A1 | 7/2008 | Sanders et al. | |
| 2009/0032465 A1* | 2/2009 | Baumgarten et al. | 210/637 |
| 2010/0147763 A1* | 6/2010 | Tsou et al. | 210/500.21 |
| 2011/0011799 A1* | 1/2011 | Rozendal et al. | 210/620 |
| 2011/0123902 A1* | 5/2011 | Zhang et al. | 429/506 |

FOREIGN PATENT DOCUMENTS

WO    0117664 A1    3/2001

OTHER PUBLICATIONS

Van Zyl, A. J., et al., Application of new sulfonated ionomer membranes in the separation of pentene and pentane by facilitated transport, Journal of Membrane Science, v 137, n 1-2, p. 173-185, Dec. 24, 1997.

Choi, H.W., et al., Highly selective facilitated transport membranes for isoprene/n-pentane separation, Journal of Membrane Science 279(1/2) 2006 p. 403-409 Elsevier.

Sonnenschein, M.F., Hollow fiber microfiltration membranes from poly(ether ether ketone) (PEEK), Journal of Applied Polymer Science, v 72, n 2, p. 175-181, Apr. 11, 1999.

Zhao, C., et al., Synthesis of the block sulfonated poly(ether ether ketone)s (S-PEEKs) materials for proton exchange membrane, Journal of Membrane Science 280(1/2) 2006 p. 643-650.

(Continued)

*Primary Examiner* — Tam M Nguyen
(74) *Attorney, Agent, or Firm* — Arthur D Gooding

(57) ABSTRACT

Processes for olefin/paraffin separation utilizing porous, hydrophobic poly(ether ether ketone) (PEEK) membranes are provided. In accordance with an exemplary embodiment, a process for olefin/paraffin separation comprises providing a porous membrane formed of PEEK polymer functionalized with hydrophobic groups, the porous membrane having a first surface and a second surface. The first surface of the porous membrane is contacted with a feed comprising an olefin and a paraffin and a permeate is caused to flow from the second surface of the porous membrane. The permeate has a concentration of the paraffin that is higher than a concentration of the paraffin of the feed.

20 Claims, 3 Drawing Sheets

OTHER PUBLICATIONS

Chng, M.L., et al., Enhanced propylene/propane separation by carbonaceous membrane derived from poly (aryl ether ketone)/2,6-bis(4-azidobenzylidene)-4-methyl-cyclohexanone interpenetrating network, Carbon, v 47, n 7, p. 1857-1866, Jun. 2009.

Su, Y.H., et al., Increases in the proton conductivity and selectivity of proton exchange membranes for direct methanol fuel cells by formation of nanocomposites having proton conducting channels, Journal of Power Sources 194(1) 2009 p. 206-213.

Nymejer, K., et al., Super selective membranes in gas—liquid membrane contactors for olefin/paraffin separation, Journal of Membrane Science, vol. 232, Issues 1-2, Mar. 15, 2004, pp. 107-114.

Mehta, R. H., et al., Microporous membranes based on poly (ether ether ketone) via thermally-induced phase separation, Journal of Membrane Science, vol. 107, 2004, pp. 93-106.

* cited by examiner

PROCESSES FOR OLEFIN/PARAFFIN SEPARATION UTILIZING POROUS, HYDROPHOBIC POLY(ETHER ETHER KETONE) MEMBRANES

FIELD OF THE INVENTION

The present invention generally relates to gas separation processes, and more particularly relates to processes for olefin/paraffin separation utilizing porous, hydrophobic poly(ether ether ketone) membranes.

BACKGROUND OF THE INVENTION

Light olefins, such as propylene and ethylene, are produced as co-products from a variety of feedstocks in a number of different processes in the chemicals, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have advantages of both low capital cost and high-energy efficiency compared to conventional separation methods for olefin/paraffin separations such as propylene/propane and ethylene/ethane separations. Three main types of membranes have been reported for olefin/paraffin separations. They are facilitated transport membranes, polymer membranes, and inorganic membranes. Facilitated transport membranes, or ion exchange membranes, which use silver ions as a complexing agent, have very high olefin/paraffin separation selectivity and high olefin fluxes. However, poor chemical stability due to carrier poisoning currently limit practical applications of the facilitated transport membranes.

Separation of olefin from paraffin via conventional polymer membranes has not been commercially successful due to inadequate selectivities and permeabilities of the polymer membrane materials, as well as due to plasticization issues. Polymers that are more permeable are generally less selective than are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success. In addition, polymer membranes based on solution-diffusion separation mechanisms frequently suffer from plasticization of the polymer chains by the sorbed condensable penetrate molecules such as ethylene and propylene. Plasticization of the polymer, represented by the membrane structure swelling and a significant increase in the permeabilities of all components in the feed, occurs above the plasticization pressure when the feed gas mixture contains condensable gases, resulting in the decrease in selectivity. On the other hand, inorganic membranes, such as carbon molecular sieve and zeolite inorganic membranes, potentially offer adequate selectivities. However, they are brittle and currently too costly to be commercially useful for large scale applications.

Accordingly, it is desirable to provide processes for olefin/paraffin separation using membranes that have high selectivity and that are highly permeable. In addition, it is desirable to provide processes for olefin/paraffin separation using porous, hydrophobic poly(ether ether ketone) membranes. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Processes for olefin/paraffin separation utilizing porous, hydrophobic poly(ether ether ketone) (PEEK) membranes are provided. In accordance with an exemplary embodiment, a process for olefin/paraffin separation comprises providing a porous membrane formed of PEEK polymer functionalized with hydrophobic groups, the porous membrane having a first surface and a second surface. The first surface of the porous membrane is contacted with a feed comprising an olefin and a paraffin and a permeate is caused to flow from the second surface of the porous membrane. The permeate has a concentration of the paraffin higher than a concentration of the paraffin of the feed.

In accordance with another exemplary embodiment, a process for separating an olefin and a paraffin comprises providing a hydrophobic PEEK membrane having an average pore size of about 0.5 nm. The hydrophobic PEEK membrane has a first surface and a second surface. The first surface of the hydrophobic PEEK membrane is contacted with a feed comprising the olefin and the paraffin. A permeate is removed from the second surface of the hydrophobic PEEK membrane. The permeate has a concentration of the paraffin that is higher than a concentration of the paraffin of the feed.

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The various embodiments of the present invention provide a process for the separation of paraffin and olefin, such as, for example, in gaseous streams produced from stream cracking, catalytic cracking, the dehydration of paraffins, and the like. The process utilizes a poly(ether ether ketone) (PEEK) membrane that is highly permeable but also highly selective to paraffin, thus permitting paraffin to permeate the membrane at a much higher rate than the olefin. The membrane can take a variety of forms suitable for a particular application. For example, the membrane can be in the form of a flat sheet, hollow tube or fiber, spiral wound, and the like. In this regard, various embodiments of the process contemplated herein can be used to replace C2 and C3 splitters, as hybrid membrane distillation units for olefin purification, for recovery of olefins from polypropylene vent streams or from fluid catalytic cracking (FCC) off-gas streams, or the like. The process can also be used for the production of polymer grade propylene, thus offering significant energy, capital, and operating cost savings compared to conventional distillation.

Figure 1:
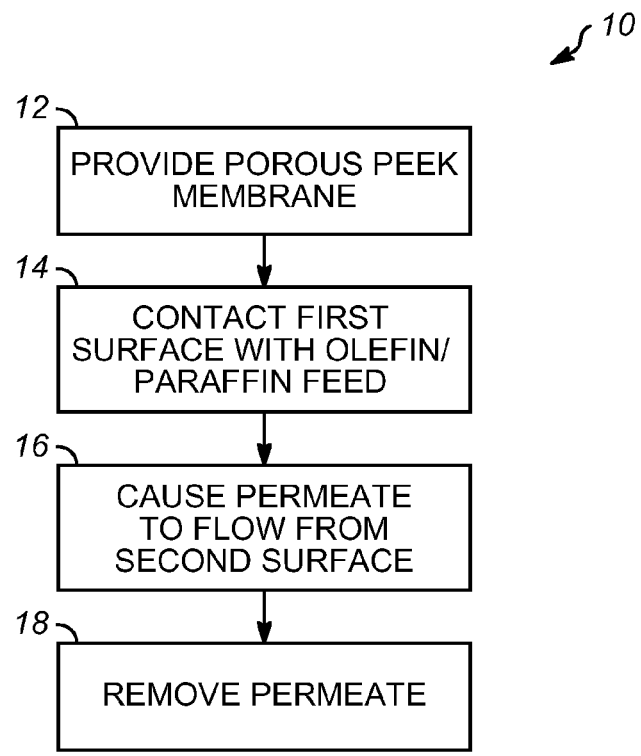
FIG. 1 is a flow chart of a process for olefin/paraffin separation in accordance with an exemplary embodiment of the present invention.

FIG. 1 is a flow chart of a process 10 for olefin/paraffin separation in accordance with an exemplary embodiment of the present invention. The process 10 begins by providing a porous, hydrophobic membrane formed from poly(ether ether ketone) (step 12). PEEKs are a class of semi-crystalline thermoplastics with thermal and chemical stability. PEEK polymers are insoluble in almost all common solvents at room temperatures, thus making PEEK polymers attractive materials for membranes useful in refinery and petrochemical processing. The porous, hydrophobic PEEK membrane useful in the various embodiments of the process contemplated herein can comprise any PEEK polymer in which the ketone groups in the backbone of the PEEK polymer have been reacted with a functionalized primary amine. The functionalized primary amine is a primary aliphatic amine or a substituted hydrazine that contains one or more hydrophobic groups including, but not limited to, siloxane, perfluoro hydrocarbon groups, and non-polar hydrocarbon groups that are covalently bonded to the backbone of the PEEK polymer. The hydrophobic groups of the primary amine cause the PEEK membrane to be more permeable to paraffin than to olefin, as paraffin is more hydrophobic than olefin. Methods for forming porous, hydrophobic PEEK membranes are known in the art and are described, for example, in U.S. Pat. No. 7,176,273 B2, issued on Feb. 13, 2007 to Yuan et al., and Mehta, et al., "Microporous Membranes Based On Poly (Ether Ether Ketone) Via Thermally-Induced Phase Separation," *J. Membr. Sci.,* 107 (1995), pp. 93-106, which are hereby incorporated in their entirety by reference.

The hydrophobic PEEK membranes are asymmetric membranes having a pore size of no more than about 0.5 nanometers (nm). Asymmetric membranes are characterized by a thin, dense, selectively semipermeable surface and a less dense void-containing, non-selective support region, with pore sizes ranging from large in the support region to very small proximate to the semipermeable surface. Because the olefin molecules are smaller than the paraffin molecules, the small pore size of the polymer further facilitates the higher selectivity of paraffin over olefin through the membrane. In another embodiment of the present invention, the porous, hydrophobic PEEK membrane can be post-treated, that is, the treatment is performed after the membrane is formed, by coating at least the thin, dense, selectively semipermeable surface of the membrane with a layer of high-permeability, hydrophobic polymer, such as, for example, a silicone rubber polymer. The high-permeability, hydrophobic polymer coating further reduces the pore size of the hydrophobic PEEK membrane, thus providing enhanced selectivity for olefin/paraffin separation without a dramatic decrease in paraffin permeance. Methods for coating PEEK membranes are known in the art and are described, for example, in U.S. Pat. No. 6,368,382 B1 issued on Apr. 9, 2002 to Jeffrey J. Chiou, which is hereby incorporated in its entirety by reference.

Figure 2:
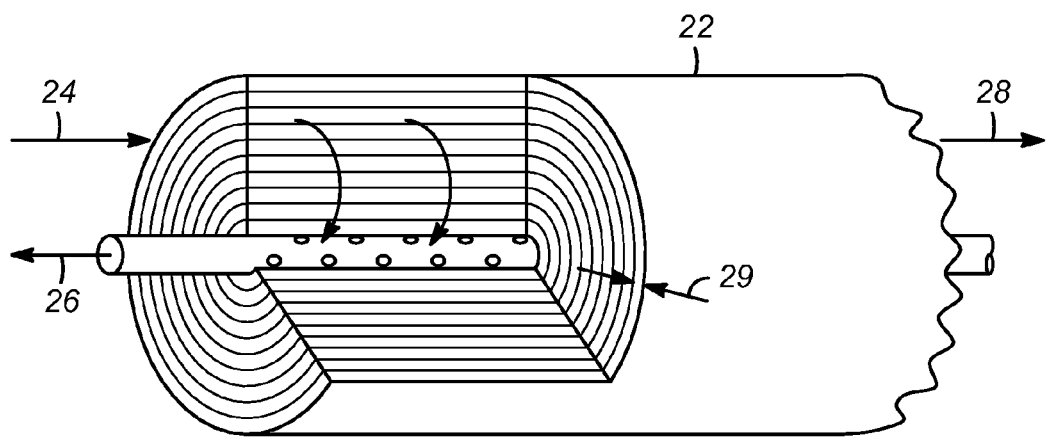
FIG. 2 is a schematic illustration of a spiral-wound, porous, hydrophobic poly(ether ether ketone) membrane module for use in the process of FIG. 1, in accordance with an exemplary embodiment of the present invention.
Figure 3:
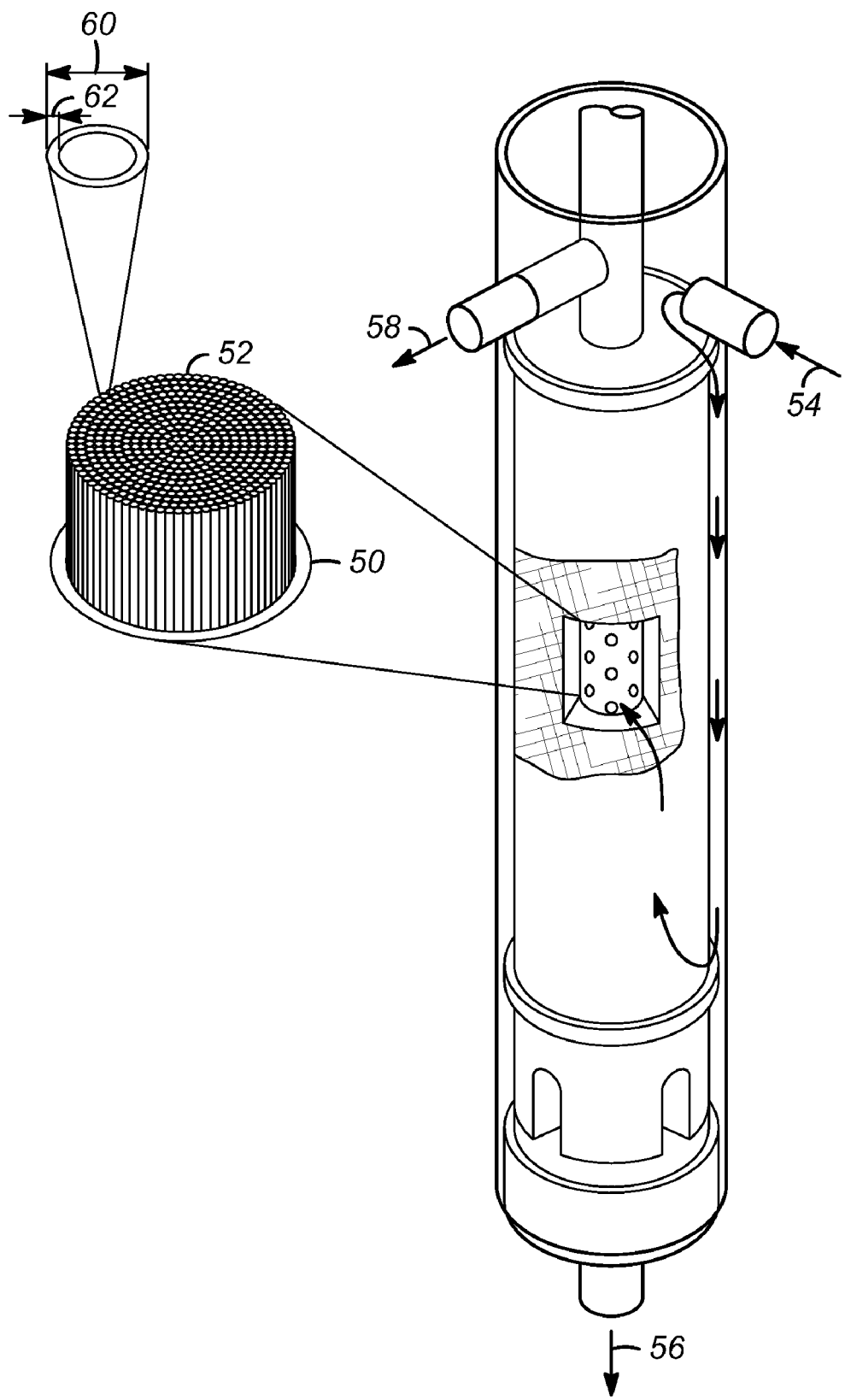
FIG. 3 is a schematic illustration of a hollow fiber, porous, hydrophobic poly(ether ether ketone) membrane module for use in the process of FIG. 1, in accordance with an exemplary embodiment of the present invention.
Figure 4:
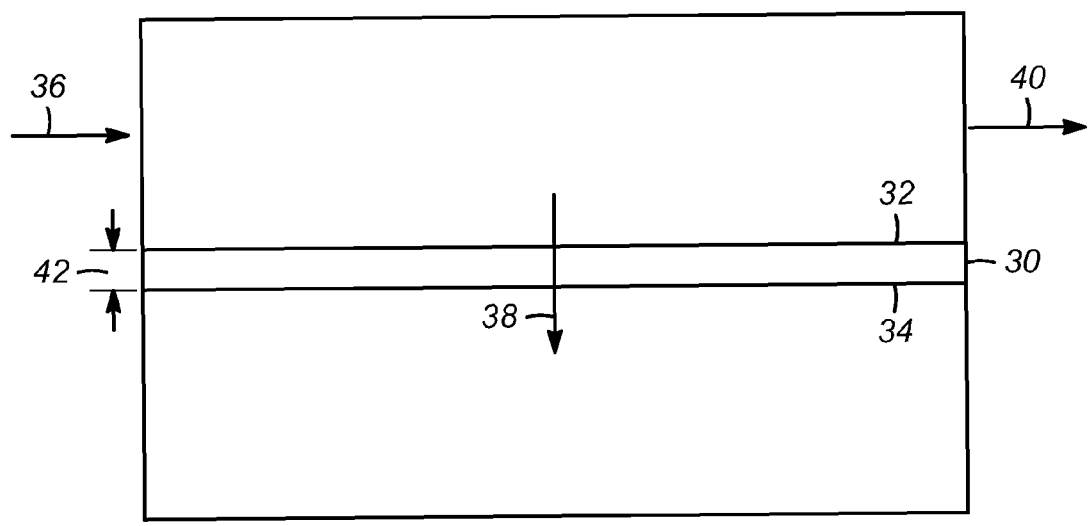
FIG. 4 is a schematic illustration of a flat-sheet, porous, hydrophobic poly(ether ether ketone) membrane module for use in the process of FIG. 1, in accordance with an exemplary embodiment of the present invention.

The porous, hydrophobic PEEK membranes useful in the processes contemplated herein can be in any form suitable for a desired application. For example, the membranes can be in the form of hollow fibers or tubes, flat sheets, spiral wound, corrugated sheets, and the like. The form of the membrane may depend upon the nature of the membrane itself and the ease of manufacturing the form. The membrane can be assembled in a separator in any suitable configuration for the form of the membrane and the separator may provide for co-current, counter-current, or cross-current flows of the feed on the retentate and permeate sides of the membrane. In one exemplary embodiment, as illustrated in FIG. 2, a membrane 22 in a spiral wound module is in the form of flat sheet having a thickness 29 of from about 30 to about 100 μm. A feed 24 contacts a first surface of the membrane 22, a permeate 26 permeates the membrane 22 and is removed therefrom, and a retentate 28, not having permeated the membrane, also is removed therefrom. In another exemplary embodiment, as illustrated in FIG. 3, a membrane 50 in a hollow fiber module is in the form of thousands, tens of thousands, hundreds of thousands, or more, of parallel, closely-packed hollow fibers or tubes 52. In one embodiment, each fiber has an outside diameter 60 of from about 200 micrometers (μm) to about 700 millimeters (mm) and a wall thickness 62 of from about 30 to about 200 μm. In operation, a feed 54 contacts a first surface of the membrane 50, a permeate 56 permeates the membrane and is removed therefrom, and a retentate 58, not having permeated the membrane, also is removed therefrom. Referring to FIG. 4, and as discussed in more detail below with reference to FIG. 1, a membrane 30 can be in the form of flat sheet having a thickness 42 in the range of from about 30 to about 200 μm.

Referring to FIGS. 1 and 4, the process 10 continues by contacting a first surface 32 of the membrane 30 with an olefin/paraffin feed 36 (step 14). While process 10 of FIG. 1 is described with reference to membrane 30 of FIG. 4 for convenience, it will be appreciated that process 10 is not so limited and, as discussed above, can be performed utilizing any suitable membrane form. The olefin may comprise, for example, propylene or ethylene and the paraffin may comprise propane or ethane, respectively. The olefin/paraffin feed comprises a first concentration of olefin and a first concentration of paraffin depending on the application for which the membrane separation is used. For example, a propane dehydrogenation process typically provides a feed containing about 35 mass percent propylene whereas feed from an FCC unit generally contains about 75 mass percent propylene. The flow rate and temperature of the olefin/paraffin feed 36 have those values that are suitable for a desired application.

Next, a permeate 38 is caused to flow through the membrane 30 and from a second surface 34 of the membrane 30 (step 16). Because the porous, hydrophobic PEEK membrane is more selective to the paraffin than to the olefin, the permeate 38 has a concentration of paraffin that is higher than the concentration of the paraffin in the feed 36. In addition, while some olefin may permeate through the membrane, the permeate 38 has a concentration of olefin that is less than the concentration of the olefin in the feed. The permeate can then be removed from the second surface 34 of the membrane (step 18). As the permeate 38 passes through the membrane 30, a retentate 40, or residue, which has not permeated the membrane, is removed from the first surface 32 of the membrane 30. The retentate 40 has a concentration of paraffin that is lower than the concentration of paraffin in the feed 36 and lower than the concentration of the permeate 38. The retentate 40 also has a concentration of olefin that is higher than a concentration of olefin that is in the feed. In one exemplary embodiment, the concentration of the olefin in the retentate is 99.5 mass percent.

The following is an exemplary embodiment of a process for olefin/paraffin separation using a porous, hydrophobic PEEK membrane, as contemplated herein. The example is provided for illustration purposes only and is not meant to limit the various embodiments of the processes in any way.

EXAMPLE

A membrane comprising approximately ten thousand (10,000) fibers formed of porous, hydrophobic PEEK material was provided. The porous hydrophobic PEEK membrane was formed by reacting a PEEK polymer with a functionalized primary amine comprising perfluoro hydrocarbon. Each of the fibers of the membrane were approximately 0.91 meters (36 inches) long and had an inside diameter of 360 μm and a wall thickness of 70 μm.

A first surface of the membrane was contacted with an olefin/paraffin feed at a flow rate of about 0.054 m$^3$/hr (2 ft$^3$/hr). The feed comprised 40 moles percent (mol %) propylene and 60 mol % propane. The feed was at a temperature of 50° C. and under a pressure of 1.2 megapascals (MPa) (174 pounds-per-square-inch (psi)). The resulting permeate flowing and removed from a second surface of the membrane had a concentration of propylene of 5 mol % and a concentration of propane of 95 mol %.

The various embodiments of a process for the separation of paraffin and olefin have thus been provided. The process utilizes a poly(ether ether ketone) membrane that is highly permeable and highly selective to paraffin, thus permitting paraffin to permeate the membrane at a much higher rate than the olefin. The membrane can take a variety of forms suitable for a particular application. For example, the membrane can be in the form of a flat sheet, hollow tube or fiber, spiral wound, and the like. In this regard, various embodiments of the process contemplated herein can be used to replace C2 and C3 splitters, as hybrid membrane distillation units for olefin purification, or for recovery of olefins from polypropylene vent streams or from FCC off-gas streams. Thus, the process can offer significant energy, capital, and operating cost savings compared to conventional distillation.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for olefin/paraffin separation, the process comprising the steps of:
   providing a porous membrane formed of poly(ether ether ketone) (PEEK) polymer functionalized with hydrophobic groups, the porous membrane having a first surface and a second surface;
   contacting the first surface of the porous membrane with a feed comprising an olefin and a paraffin; and
   causing a permeate to flow from the second surface of the porous membrane, the permeate having a concentration of the paraffin higher than a concentration of the paraffin of the feed.

2. The process of claim 1, wherein the step of providing the porous membrane comprises providing the porous membrane formed of a PEEK polymer functionalized with hydrophobic groups selected from the group consisting of siloxanes, perfluoro hydrocarbon groups, and non-polar hydrocarbon groups.

3. The process of claim 1, wherein the step of providing the porous membrane comprises providing the porous membrane having a pore size of no more than about 0.5 nm.

4. The process of claim 1, wherein the step of providing the porous membrane comprises providing the porous membrane having the first surface that has been coated with a layer of high-permeability, hydrophobic polymer.

5. The process of claim 4, wherein the step of providing the porous membrane having the first surface that has been coated with the layer of high-permeability, hydrophobic polymer comprises providing the porous membrane having the first surface that has been coated with a silicone rubber polymer.

6. The process of claim 1, wherein the step of providing the porous membrane comprises providing a spiral wound module of a flat sheet porous membrane.

7. The process of claim 6, wherein the step of providing a spiral-wound module of a flat sheet porous membrane comprises providing the spiral-wound module of the flat sheet membrane, the flat sheet having a thickness of from about 30 to about 200 μm.

8. The process of claim 1, wherein the step of providing the porous membrane comprises providing the porous membrane in a form of a flat sheet.

9. The process of claim 8, wherein the step of providing the porous membrane in the form of the flat sheet comprises providing the porous membrane in the form of the flat sheet having a thickness of from about 30 to about 200 μm.

10. The process of claim 1, wherein the step of providing the porous membrane comprises providing a module containing a plurality of hollow fibers.

11. The process of claim 10, wherein the step of providing the module containing the plurality of hollow fibers comprises providing the module containing the plurality of hollow fibers, each fiber having an outside diameter of from about 200 to about 700 μm and a wall thickness of from about 30 to about 200 μm.

12. The process of claim 1, further comprising the step of removing the permeate from the second surface after the step of causing.

13. The process of claim 1, wherein the step of contacting the first surface of the porous membrane with the feed comprising the olefin and the paraffin comprises contacting the first surface of the porous membrane with the feed comprising propylene and propane.

14. The process of claim 1, wherein the step of contacting the first surface of the porous membrane with the feed comprising the olefin and the paraffin comprises contacting the first surface of the porous membrane with the feed comprising ethylene and ethane.

15. A process for separating an olefin and a paraffin, the process comprising the steps of:
   providing a hydrophobic poly(ether ether ketone) (PEEK) membrane having an average pore size of about 0.5 nm, the hydrophobic PEEK membrane having a first surface and a second surface;

contacting the first surface of the hydrophobic PEEK membrane with a feed comprising the olefin and the paraffin; and removing a permeate from the second surface of the hydrophobic PEEK membrane, the permeate having a concentration of the paraffin higher than a concentration of the paraffin of the feed.

16. The process of claim 15, wherein the step of providing the PEEK membrane comprises providing a membrane formed of a PEEK polymer having ketone groups that have been reacted with a functionalized primary amine, the functionalized primary amine having a hydrophobic group.

17. The process of claim 16, wherein the step of providing the membrane comprises providing the membrane formed of the PEEK polymer having ketone groups that have been reacted with the functionalized primary amine, the functionalized primary amine having a hydrophobic group selected from the group consisting of siloxanes, perfluoro hydrocarbon groups, and non-polar hydrocarbon groups.

18. The process of claim 15, wherein the step of providing the PEEK membrane comprises providing an asymmetric PEEK membrane.

19. The process of claim 15, wherein the step of providing the PEEK membrane comprises providing a porous membrane having the first surface that has been coated with a layer of high-permeability, hydrophobic polymer.

20. The process of claim 19, wherein the step of providing the porous membrane having the first surface that has been coated with the layer of high-permeability, hydrophobic polymer comprises providing the porous membrane having the first surface that has been coated with a silicone rubber polymer.

* * * * *